(12) United States Patent
Borgos et al.

(10) Patent No.: US 6,178,342 B1
(45) Date of Patent: Jan. 23, 2001

(54) SURFACE PERFUSION PRESSURE MONITORING SYSTEM

(75) Inventors: John A. Borgos, Shoreview; RIchard John Thompson, Watertown, both of MN (US)

(73) Assignee: Vasamedics, St. Paul, MN (US)

( * ) Notice: Under 35 U.S.C. 154(b), the term of this patent shall be extended for 0 days.

(21) Appl. No.: 08/859,350

(22) Filed: May 20, 1997

Related U.S. Application Data

(63) Continuation of application No. 08/118,861, filed on Sep. 9, 1993, now abandoned.

(51) Int. Cl.$^7$ .................................................. A61B 5/00
(52) U.S. Cl. ........................................... 600/322; 600/473
(58) Field of Search .................................... 600/473–478, 600/310, 322, 3, 328, 330; 356/41

(56) References Cited

U.S. PATENT DOCUMENTS

| | | | |
|---|---|---|---|
| 4,596,254 | 6/1986 | Adrian et al. | 128/666 |
| 4,597,393 | * 7/1986 | Yamakoshi et al. | 128/667 |
| 4,927,264 | * 5/1990 | Shiga et al. | 128/633 |
| 5,111,817 | * 5/1992 | Clark et al. | 128/633 |
| 5,277,181 | * 1/1994 | Mendelson | 128/665 |

OTHER PUBLICATIONS

"The Correlation Between Three Methods of Skin Perfusion Pressure Measurement: Radionuclide Washout, Laser Doppler Flow, and Photoplethysmography", Leopoldo Malvezzi, MD, John J. Castronuovo, Jr., MD, Lawrence C. Swayne, MD, David Cone, BA, and Jessie Z. Trivino, MS, Morristown, N.J., *Journal of Vascular Surgery*, pp. 823–830, vol. 15, No. 5, May, 1992.

"Laser–Doppler Flowmetry A Review of Its Application for Measuring Cerebral and Spinal Cord Blood Flow", Kai U. Frerichs and Giora Z. Feuerstein, *Molecular and Chemical Neuropathology*, pp. 55–69, vol. 12, 1990 by the Human Press Inc.

"Microvascular Blood Flow Measurement by Laser Doppler Flowmetry", Daniel J. Haumschild, Ph.D, Medical Instruments Group, TSI Incorporated, St. Paul, MN, *TSI Application Note*.

"TSI's LDV Blood Flowmeter", John A. Borgos.

"Model for Laser Doppler Measurements of Blood Flow in Tissue", R. Bonner and R. Nossal, *Applied Optics*, pp. 2097–2107, vol. 20, No. 12, Jun. 15, 1991.

"In Vivo Evaluation of Microcirculation by Coherent Light Scattering", M. D. Stern, *Nature*, pp. 56–58, vol. 254, Mar. 6, 1975.

"Blood–Flow Measurements of Injured Peripheral Nerves by Laser Doppler Flowmetry", C. M. Barone, D. F. Jimenez and A. Frempog–Bodeau, *Journal of Reconstructive Microsurgery*, pp. 319–323, vol. 8, No. 4, Jul., 1992.

"Simultaneous Measurement of Skin Blood Flow by the Transient Termal–clearance Method and Laser Doppler Flowmetry", M. Nitzan, S. L. E. Fairs and V. C. Roberts.

"Laser Doppler Flowmetry Evaluation of Burn Wound Depth", T. J. O'Reilly, MD, R. J. Spence, MD, R. M. Taylor, MD and J. J. Scheulen, PA, *The Journal of Burn Care & Rehabilitation*, pp. 1–6, vol. 10, No. 1, Jan./Feb., 1989.

(List continued on next page.)

*Primary Examiner*—Robert L. Nasser

(57) ABSTRACT

A blood perfusion pressure monitor which measures blood content within an observation volume as a function of applied pressure, to determine the skin perfusion pressure at a location on a patient.

4 Claims, 5 Drawing Sheets

OTHER PUBLICATIONS

"Evaluation of Skin Blood Flow and Venoarteriolar Response in Patients with Diabetes and Peripheral Vascular Disease by Laser Doppler Flowmetry", Gianni Belcaro, MD, Spiros Vasdekis, MD, Alexander Rulo, MD and Andrew N. Nicolaides, MS *Angiology—The Journal of Vascular Diseases*, pp. 953–957, vol. 40, No. 11, Nov., 1989.

"Combined Evaluation of Postphlebitic Limbs by Laserdoppler Flowmetry and Transcutaneous P02/PC02 Measurements", Messmethoden—Diagnostic Methods, G. Belcaro, A. Rulo, S. Vasdekis, M. A. Williams and A. N. Nicolaides, *VASA*, Band 17, 1988, Heft 4.

"Laser–Doppler Assessment of Brain Microcirculation: Effect of Systemic Alterations", Rowan L. Haberl, Marcia L. Heizer, Anthony Marmarou and Earl F. Ellis, *The American Physiological Society*, pp. H1247–H1254.

* cited by examiner

SURFACE PERFUSION PRESSURE MONITORING SYSTEM

This is a Continuation of application Ser. No. 08/118,861, filed Sep. 9, 1993, now abandoned.

1. TECHNICAL FIELD

The present invention relates to a blood perfusion monitor which may be used to determine the skin perfusion pressure of a portion of a patient body such as a limb. The apparatus is used to determine the applied pressure which corresponds to the cessation or resumption of localized blood flow in the limb or other anatomic structure.

2. BACKGROUND

Laser Doppler blood flow monitors have been used in conjunction with pneumatic cuffs to determine localized blood flow see for example *The Correlation between Three Methods of Skin Perfusion Measurement* (J. Vasc Surg 1992;15:823–30). Laser Doppler blood flow monitors are known from U.S. Pat. No. 4,596,254 among others. Devices of this type use a fiber optic wave guide to scatter coherent light off of both, moving particles, mainly red blood cells (RBC), and stationary vascular structures. The back scattered radiation is conducted by a separate fiber optic wave guide to a photodetector. The back scattered laser light returned to the photodetector is frequency shifted by the moving particles in accordance with the Doppler effect. Consequently the photodetector signal includes an AC signal component related to the number of RBC and their velocity. This AC signal is superimposed on a DC offset signal which depends in part on the intensity of the coherent light source and the geometry of the multiple fiber detector. Blood volume or hematocrit information and blood velocity information can be extracted from the composite photodetector signal.

Blood flow information is computed by multiplying the blood velocity data by the blood volume data. One problem with the use of flow monitors for perfusion measurements or studies is that the blood flow product value is very sensitive to small errors in measured blood velocity or measured blood volume. This property of flow measurement makes the technique problematical for monitoring skin perfusion pressure.

SUMMARY

By contrast, the perfusion pressure monitor of the present invention does not measure blood flow itself. The perfusion pressure monitor of the present invention measures the "amount" of moving blood contained within a microvascular observation volume in percent tissue hematocrit. This percent hematocrit measurement is taken as a function of applied pressure. The optical probe defines an observation volume in the skin near the surface of the patient. A pressure cuff is used to apply pressure to the patient near the optical probe.

The skin perfusion pressure measurement involves the measurement of the pressure within the cuff at the moment that blood within the observation volume is either stationary or expressed from the observation volume. The pressure corresponding to the change in effective percent hematocrit is a significant diagnostic indication for many medical procedures.

BRIEF DESCRIPTION OF THE DRAWINGS

An illustrative and exemplary perfusion pressure monitor is shown in the accompanying drawings, wherein like reference numerals refer to identical structure throughout and in which.

DETAILED DESCRIPTION

Figure 1:
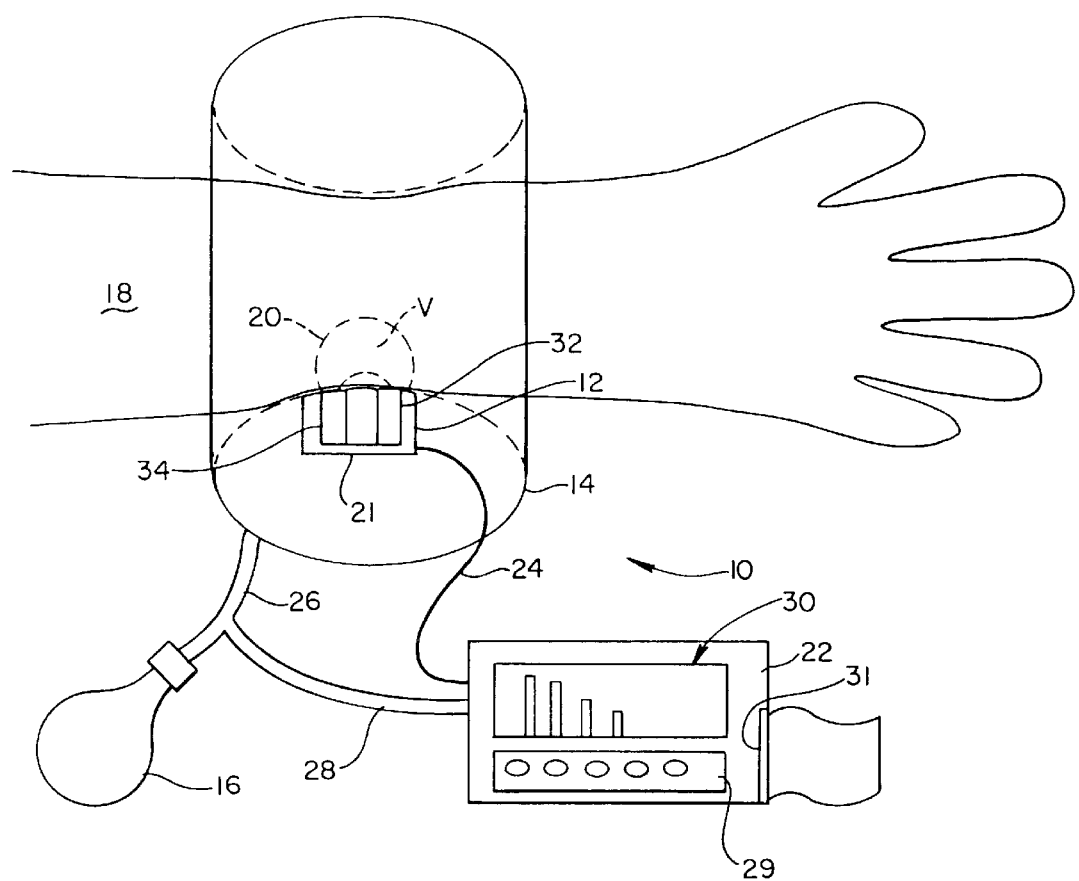
FIG. 1 is a schematic representation of the perfusion pressure monitor in use with a patient.

FIG. 1 is a schematic diagram which depicts a representative but not limiting perfusion pressure monitoring system 10. The perfusion pressure monitoring system 10 includes a optical probe 12 located inside of a pressure cuff 14. The user may squeeze an inflation bulb 16 which inflates the pressure cuff 14 through tube 26 and positions the optical probe 12 against the skin of the patient's limb 18. The pressure cuff and inflation bulb must be able to supply a sufficiently high pressure (above systolic) to stop local blood flow at the site of the optical probe 12. The display instrument 22 is coupled to both the optical probe 12 via a fiber optic cable 24, and to the inflation bulb 16 through a tube 28.

The optical probe 12 monitors the number of moving red blood cells moving into or out of the observation volume 20, without regard to their velocity. The "number" of red blood cells detected within the control volume 20 is expressed as a percent hematocrit and displayed on the display 30 of the perfusion pressure display instrument 22. The percent hematocrit value is shown as both a numeric value (from 0% to 10%) and a bar graph on the Y-axis (in three ranges) of the instrument display 30. The perfusion pressure display instrument 22 also measures the pressure within the cuff 14 and displays the applied cuff pressure in millimeters of mercury on the X-axis of the display and as a numeric value on the display (from 0 to 200 mm Hg in two ranges). A moving bar along the X-axis shows the operator which bin and cuff pressure that is currently being measured. Other display formats including continuous line formats are within the scope of the invention.

The schematic optical probe 12 shown on FIG. 1 includes at least a laser transmitter fiber 32 and at least one receiver fiber 34. In operation, coherent light supplied from a solid state, or other laser device within the perfusion pressure display instrument 22 is conducted to the transmitter fiber 32 which is in intimate contact with the patients skin through the transparent pressure cuff 14 bladder. Photons emitted from the transmit fiber 32 are scattered by the patients tissues. A small portion (less than 5%) of the emitted photons are collected by the receiver fiber 34. The optical apertures of the fibers establish the volume of tissue that is monitored. Typically a single transmitter fiber is used with a pair of receiver fibers. The nominal fiber core diameter is on the order of 50 to 100 microns and is used to establish an observation volume of approximately one to two cubic millimeters. A suitable optical transducer is the P440 or P430 transducer device manufactured by Vasamedics of St Paul, Minn.

Figure 6:
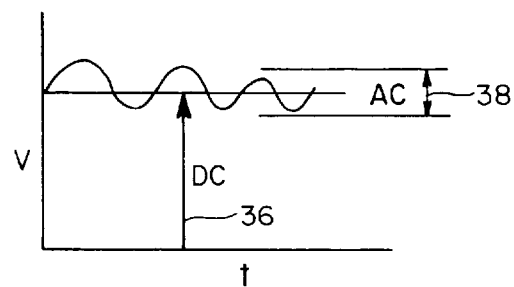
FIG. 6 is a schematic waveform diagram illustrating the photodetector output signal.

The back-scattered photons are frequency shifted by the motion of the RBCs. The collected photons are carried to the perfusion pressure display instrument 22 via cable 24 where they impinge on a photodiode. The photodiode voltage contains both frequency and power information. The frequency information is related to RBC velocity while the power information is related to the blood volume. An idealized and simplified waveform is shown as FIG. 6. The DC offset voltage 36 results from the total number of photons received by the receive fiber 34. The AC component 38 of the signal results from the mixing of frequency shifted photons with photons from stationary structures. If the number of RBCs within the observation volume increases then the magnitude of the AC component will increase while the DC offset will remain constant. The AC component increases since more returned photons undergo a Doppler shift. The DC component remains constant since the total number of photons does not change. Therefore the ratio of the AC to the DC component of the signal indicates the "volume" of moving blood in the observation volume of tissue. It is common to indicate the RBC fraction of a unit volume of blood as a percent hematocrit, or percent volume. This type of hematocrit measurement is preferably computed with both analog and digital signal processing. For example it is preferred to convert the DC and AC signals to their RMS equivalent through analog processing. It is these values which are presented to the A/D converter. The microprocessor then may square these digitized values prior to forming the ratio. The ratio value may be scaled by an empirically derived scaling factor which depends on the gain distribution throughout the signal processing paths.

Figure 2:
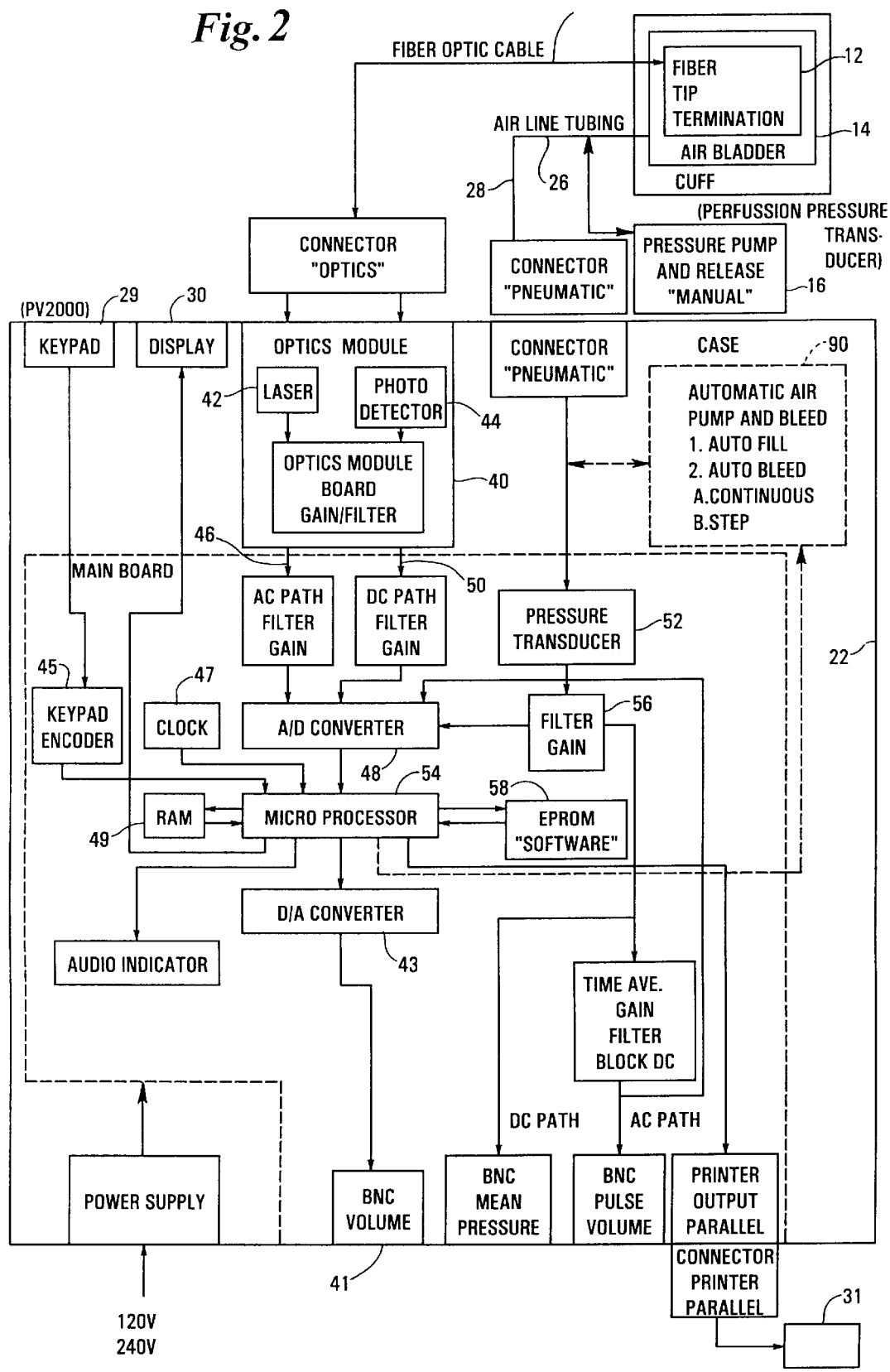
FIG. 2 is a schematic representation of the hardware architecture of the perfusion pressure monitor.

FIG. 2 shows an illustrative hardware architecture for carrying out the invention. It should be understood that many modifications to the hardware structure may be made without departing from the scope of the invention. In general the laser 42 and photodetector 44 are located in a shielded enclosure 40. The enclosure 40 is use to isolate the high gain components from the remainder of the circuitry. After suitable buffering, filtration and amplification the AC signal component from the photodetector 44 in the enclosure 40 is coupled to an A/D converter 48 through signal path 46. The DC signal component 36 is coupled through signal connection 50 to the A/D converter 48. It is preferable to bandpass filter the AC and DC signal components to eliminate out of band noise. A suitable empirically derived bandpass for the DC component is DC to approximately 5 Hertz. A suitable empirically derived bandpass for the AC component is 70 Hertz to 1.7 K Hertz.

The cuff pressure is communicated to a pressure transducer 52, which is in turn coupled to the A/D converter 48 after appropriate signal conditioning in block 56. The A/D converter 48 operates under software control and provides digitized signals to the microprocessor 54. The software for operating the microprocessor 54 is stored in the EPROM 58. The microprocessor portion of the system also includes a RAM memory 49 system clock 47, and keypad encoder 45.

In general the user interacts with the system 10 through the keypad 29, display 30, printer 31, and the inflation bulb 16. In operation the user selects the skin perfusion pressure methodology through the keyboard 29. Next the user inflates the inflation bulb to pressurize the cuff 14. During this time the user may monitor the pressure in the cuff in real time and also monitor the corresponding percent hematocrit measurement on the display. The test begins at a high pressure sufficient to reduce the displayed percent hematocrit below .1 percent or lower. Next the user deflates the cuff slightly. In response, the instrument 10 opens a new display bin corresponding to the lower pressure and displays the average percent hematocrit corresponding to this reduced pressure. After a user selected delay the display prompts the user through an audible indicator to lower the pressure again to make the next hematocrit measurement. The interaction between the user and the instrument results in the collection of skin perfusion data as a function of cuff pressure.

It should also be apparent that the stepwise sequence which involves the user to select the pressure may be automated by an appropriate pneumatic system 90 under microprocessor control. The automatic system 90 includes a valve operated by the microprocessor which admits air pressure to the cuff, or which vents air from the cuff. In operation the microprocessor will establish sequential cuff pressure set points and match the cuff pressure to the set point. Next the hematocrit measurement will be made before moving to the next set point pressure.

Although the principal interaction is with the display 30 during the test, the system also provides a hardcopy report from the printer 31 and also provides a scaled analog voltage proportional to the measured hematocrit value trough a D/A converter and analog output port 41.

Figure 7A:
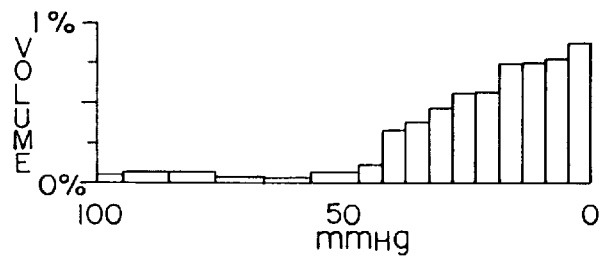
FIG. 7 is broken into two panels labeled as FIG. 7A and FIG. 7B each of which is a schematic diagram illustrating the output display of the instrument.
Figure 7B:
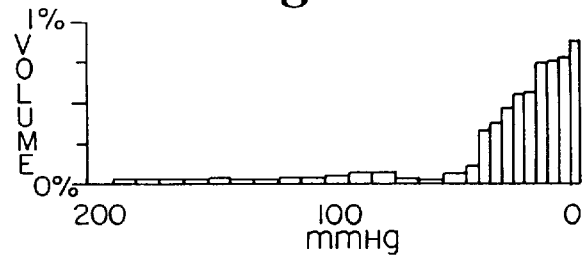

A representative display is presented as FIG. 7A. As seen in FIG. 7A there is a distinct rise in percent hematocrit at approximately forty five millimeters of mercury. The diagnostician will typically take this pressure as the value for the skin perfusion pressure. In FIG. 7B The same test data is shown at a different resolution. Although the interaction described above requires the user to adjust the cuff pressure. It is contemplated that the pressure determination process may be fully automated.

Figure 3:
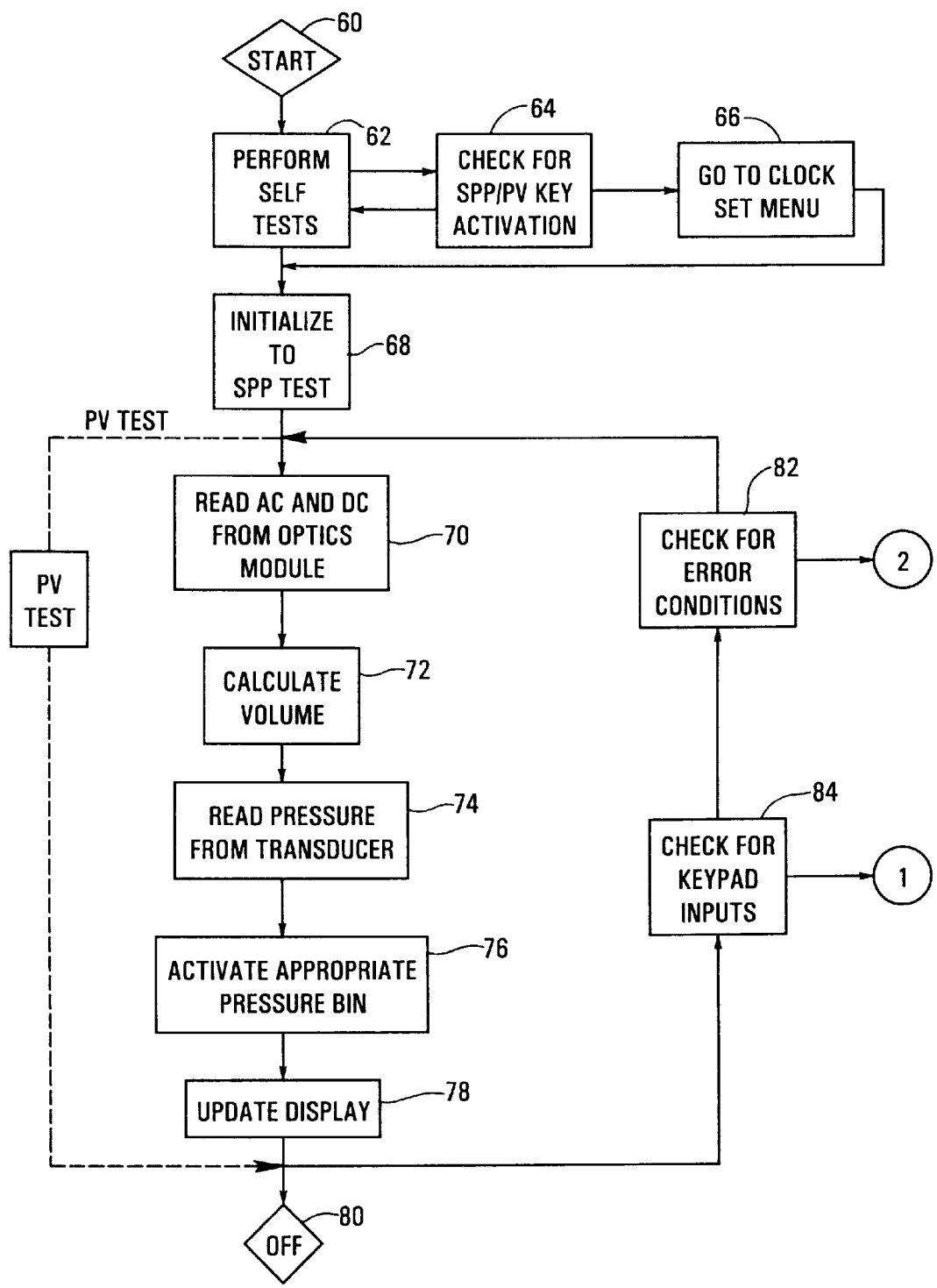
FIG. 3 is a flowchart representing the operation of the perfusion pressure monitor.
Figure 4:
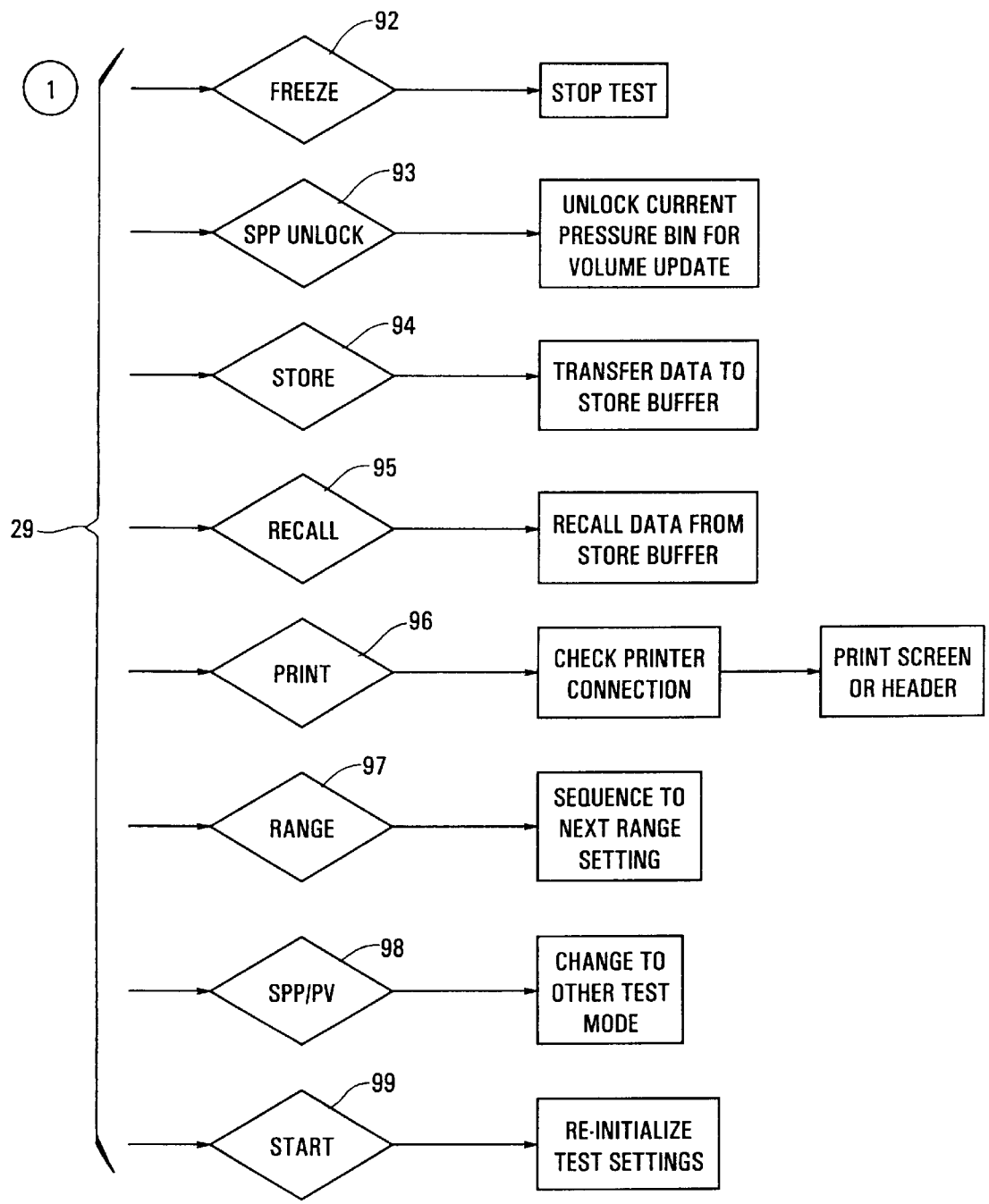
FIG. 4 is a flowchart representing the operation of the perfusion pressure monitor.
Figure 5:
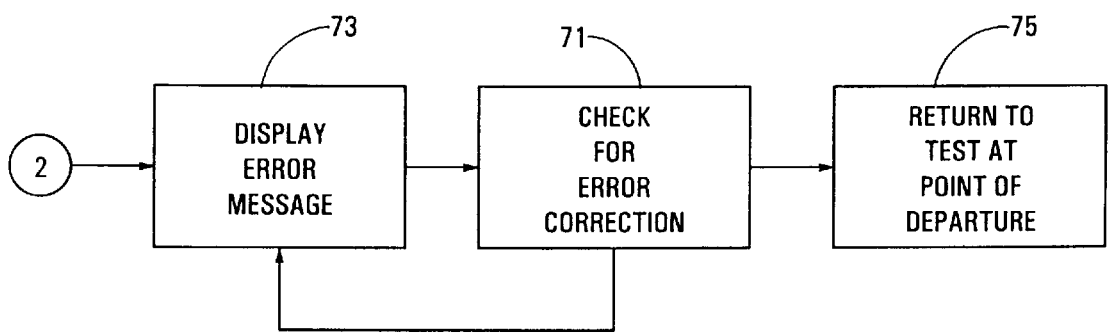
FIG. 5 is a flowchart representing the operation of the perfusion pressure monitor.

FIG. 3 is a system level flowchart setting forth illustrative software processes for carrying out the invention. Start block 60 represents initial power up of the perfusion pressure monitoring system 10. In block 62 the system preforms various self checks to test the integrity of the overall system. After completion of the self test the processor periodically interrogates the SPP/PV key. This key represent a user choice between the skin perfusion pressure mode (SPP) of operation and a pulse volume mode (PV). As previously described the skin perfusion pressure mode is the subject of this invention and the PV mode is not. However for completeness, in the PV mode the cuff pressure is displayed against time. The resultant pulsatile waveform results from the patient's heart beat. The morphology of the waveform may be used as a diagnostic aid by the physician. With the SPP mode selected via key 98 (FIG. 4) the program moves to block 66 where the clock set menu is activated. In general the test measurement made by the instrument are displayed on the display and they are also provide to a printer and annotated with the test time and date. The clock set menu is used to initialize the real time clock with the correct time and date as seen in FIG. 7. Next the system moves to block 68 where the system is initialized for the SPP test methodology. In block 70 the microprocessor reads the AC and DC signal values from the A/D converter. In block 72 the percent hematocrit is calculated for the observation volume. This calculation extracts the root of the squared of the ratio of the Ac to the DC signal values. This is taken as the measure of the percent hematocrit and does not include a RBC velocity term. In block 74 the corresponding pressure for the percent hematocrit measurement is taken. In block 76 the display is formed by displaying the measured percent hematocrit against the cuff pressure. In block 78 the display is refreshed to update the measured values of the skin perfusion pressure. After the display is updated in block 78 the program flow goes to block 84 where the microprocessor checks for keypad 29 inputs, and also checks for error conditions in block 82. The keypad 29 keys (items 92 to 99) are set forth in FIG. 4 along with their corresponding actions. For example depressing "freeze" key 92 results in stopping the test. In the event of error conditions the program flow moves to FIG. 5 where the error conditions are displayed to the user. For example once an error condition is detected the block 73 displays the appropriate error message on the display 30. After the error condition is corrected by the user the block 71 will pass program flow to the test in progress via block 75.

Although an exemplary embodiment of the perfusion pressure monitor 10 is disclosed herein many possible variations are contemplated within the scope of the invention which is to be interpreted by the following claims.

What is claimed is:

1. A perfusion pressure monitor for measuring the blood perfusion of a portion of a patient's body, said blood perfusion monitor comprising:

a laser for generating coherent radiant energy;

a laser fiber coupled to said laser for transmitting coherent radiant energy to a portion of said patient's body;

a receiver fiber for receiving coherent radiant energy back-scattered back from said patient's body;

said laser fiber and said receiver fiber together forming means for defining an observation volume within said patient's body;

a photo detector coupled to said receiver fiber for generating a doppler shifted detector signal;

means for measuring the DC component of said detector signal;

means for measuring the AC component of said detector signal;

means for computing the ratio of said AC component to said DC component forming hematocrit measurement data within said observation volume;

pressure cuff means for compressing said patient's body at the location of said observation volume;

inflation means coupled to said pressure cuff means for inflating said pressure cuff means;

means for generating pressure data from said pressure cuff means; and display means for displaying said hematocrit measurement data as a function of said pressure data.

2. The apparatus of claim 1 wherein said display means displays:

a bar graph, said bar graph having a y-axis showing the hematocrit data, said bar graph having an x-axis showing the pressure data.

3. A method for measuring perfusion within a microvascular observation volume at an observation pressure, comprising:

a. defining said microvascular observation volume at said observation pressure;

b. illuminating structures within said microvascular observation volume with a coherent source of radiation;

c. detecting backscattered radiation from said structures and generating a doppler shifted radiation signal from said backscattered radiation;

d. extracting the AC signal component from said radiation signal;

e. extracting the DC signal component from said radiation signal;

f. forming a ratio of said AC signal component to said DC signal component at said observation pressure wherein said ratio is hematocrit measurement data which corresponds to perfusion within said microvascular observation volume;

g. calculating said ratio at a plurality of observation pressures; and h. displaying said ratio as a function of said observation pressure.

4. The method of claim 3, wherein said step of calculating said ratio at a plurality of pressures calculates the ratio at a plurality of pressures as the pressure values from a higher pressure to a lower pressure.

* * * * *

UNITED STATES PATENT AND TRADEMARK OFFICE
Certificate

Patent No. 6,178,342                                                                             Patented: January 23, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: John A. Borgos, Shoreview, MN; Richard John Thompson, Watertown, MN; and John L. Castronuovo, Jr., Morristown, NJ.

Signed and Sealed this Thirtieth Day of October 2001.

*ROBERT L. NASSER*
*Acting Supervisory Patent Examiner*
*Art Unit 3736*